(12) United States Patent
Hakalehto

(10) Patent No.: US 9,458,490 B2
(45) Date of Patent: *Oct. 4, 2016

(54) METHOD AND APPARATUS FOR COLLECTING REPRESENTATIVE MICROBIOLOGICAL WATER AND LIQUID SAMPLES

(76) Inventor: Eino Elias Hakalehto, Kuopio (FI)

( * ) Notice: Subject to any disclaimer, the term of this patent is extended or adjusted under 35 U.S.C. 154(b) by 257 days.

This patent is subject to a terminal disclaimer.

(21) Appl. No.: 13/983,573

(22) PCT Filed: Feb. 3, 2012

(86) PCT No.: PCT/FI2012/000004
§ 371 (c)(1),
(2), (4) Date: Oct. 16, 2013

(87) PCT Pub. No.: WO2012/104475
PCT Pub. Date: Aug. 9, 2012

(65) Prior Publication Data
US 2014/0051115 A1 Feb. 20, 2014

(30) Foreign Application Priority Data
Feb. 3, 2011 (FI) .................................... 20110032

(51) Int. Cl.
*C12Q 1/04* (2006.01)
(52) U.S. Cl.
CPC ..................... *C12Q 1/04* (2013.01)
(58) Field of Classification Search
None
See application file for complete search history.

(56) References Cited

U.S. PATENT DOCUMENTS

| 3,793,154 A | 2/1974 | Efthymiou |
| 4,012,203 A | 3/1977 | Rosiere |
| 4,458,019 A | 7/1984 | Chrisope |
| 4,699,740 A * | 10/1987 | Bollenrath ...................... 261/93 |

FOREIGN PATENT DOCUMENTS

| WO | 9923243 A1 | 5/1999 | |
| WO | WO 2009/118445 A1 * | 10/2009 | .............. C12M 1/04 |

OTHER PUBLICATIONS

Johansson et al., Antibacterial effect of ozone on cariogenic bacterial species, Journal of Dentistry, 37 (2009) 449-453.*

* cited by examiner

*Primary Examiner* — Suzanne M Noakes
*Assistant Examiner* — Stephen Chong
(74) *Attorney, Agent, or Firm* — David Guerra

(57) ABSTRACT

With a method and equipment according to this invention the best possible growth start of hygiene indicators and other bacteria and other microbes in water samples is ensured in microbe cultivations for example on Colilert™ media using both static cultivations and bubbled cultures such as in a PMEU (Portable Microbe Enrichment Unit) type cultivation. The objective is the best possible microbiological detection value of a water sample or process sample regardless of whether the said cultivation is implemented without bubbling or other mixing or with it. The equipment and method according to the invention applies to and can be connected with automatic or manual sampling.

8 Claims, No Drawings

METHOD AND APPARATUS FOR COLLECTING REPRESENTATIVE MICROBIOLOGICAL WATER AND LIQUID SAMPLES

CROSS-REFERENCE TO RELATED APPLICATIONS

This application is an U.S. national phase application under 35 U.S.C. §371 based upon co-pending International Application No. PCT/FI2012/000004 filed on Feb. 3, 2012. Additionally, this U.S. national phase application claims the benefit of priority of co-pending International Application No. PCT/FI2012/000004 filed on Feb. 3, 2012 and Finland Application No. 20110032 filed on Feb. 3, 2011. The entire disclosures of the prior applications are incorporated herein by reference. The international application was published on Aug. 9, 2012 under Publication No. WO 2012/104475 A1.

BACKGROUND

The microbiological contamination control of waterworks and water intake works is in most cases based on the detection of certain bacterial species and strains, which indicate the state of hygiene. The hygiene control norms from several different fields list the *Escherichia coli* bacterium, and bacteria of similar kind, the so called coliform bacteria, as well as the faecal enterococci as such bacterial species and strains. The monitoring of corresponding bacteria is often central in the control procedures of the cleanliness of water supply networks. There are also risks in, for instance, the spreading of strains that are resistant to antibiotics via waste water treatment systems (Hakalehto, 2006). For example, the adhering of hygiene criterion failed in 2007 in the town of Nokia, in Finland. Waste water, which had been to some extent treated but still contained substantial amounts of different pathogens and various hygiene indicators, escaped into the clean water network. At least 10 000 persons had been exposed to the contaminated water before water use was banned, and this caused the spread of severe bacteria, viruses and protozoa originated intestinal diseases in Nokia. Additionally, various industry segments suffered financial losses due to lack of clean water. These health hazards and financial detriment could have been prevented, if the microbiological monitoring had been more sophisticated and extensive in the water intake works and waterworks.

The intensified monitoring in question could have based, for example, on the fast elucidation and detection of the same coliform and enterococci indicators that have been presented in the standards and norms of cleanliness of water. The species of bacteria in concern originate specifically from the part of the human alimentary tract in which the secretion of bile restricts the growth of many species of microbes (Hakalehto et al., 2010). This part of the intestines is in the duodenum, in the area where the most significant part of the nutrient uptake of the human organism takes place. The secretion of bile acids from the gallbladder via the duct passing through the Papilla Vateri occurs in this part of the intestines. According to a large patient database, two thirds of the bacteria occurring in this area important for the functions of the human system are coliform and enterococci bacteria. It is also probable that there exists a delicate state of equilibrium, a balanced condition between the *E-coli* and other coliform bacteria, which produce organic acids and the conforms belonging to the *Klebsiella/Enterobacter* group, which balance the production of acids, due to which, in healthy persons the pH value of the duodenum is about 6 (Hakalehto et al., 2008). This "dualistic" state of equilibrium is simulated with the Portable Microbe Enrichment Unit (PMEU) and its significance to the human system is an important reason to expect the bacteria, which take part in keeping up of this balance, to be found in the intestinal canal of almost all persons. The maintaining of this balance, therefore, has a considerable meaning to, the well-being of the intestine and, at the same time, the whole human system (Hakalehto, 2011).

When studying the microbial flora and specifically the coliform bacteria in the intestines of a new born baby, it was observed that the massive use of antibiotics slowed down, but did not prevent, bacteria belonging to the Enterobaktericeae family from settling into the intestinal canal (Pesola & Hakalehto, 2011). In addition to this, the coliform bacteria formed an essential element of the microbial flora in the intestines of new born babies who had been given nutrition of different kinds (Pesola et al. 2009). According to results of various studies, it is justifiable to use hygiene indicators in the detection of intestine-derived contamination. After an enrichment cultivation of the water samples, it is possible to analyse in more detail the origin of the microbial burden. For example, in Lake Kallavesi (Kuopio, Finland) it has been possible to typify enterococci indicators, which have been enriched in the PMEU, using a biochemical typification method, and to demonstrate clearly that the types of bacterial strains near industrial plants vary from those strain types isolated from below the treated effluent discharge of a municipal sewage treatment plant (Heitto et al., 2009; Hakalehto, 2010). In order to implement safe detection of indicator bacteria and other micro-organisms in the various stages of the production and distribution of tap water, one recommendable alternative is to build an automatic microbe control system. It is advantageous to base the microbe control system on the detection of hygiene indicators from samples whose automated or manually driven sampling frequency can be increased if the quality of water is suspected to be endangered. The decision to increase the sampling frequency of the contamination control can be based on, for instance, sensory observations or results of physiochemical measurements. The procedure can be connected to the control system which automatically changes the frequency, regional distribution and quality of sampling or other parameters. By means of an automated system (or alternatively a manual system) samples can be collected in the PMEU or corresponding equipment which, on the contrary to the PMEU does not have bubbling caused by sterile air or gas. In both cases, microbiological culture media is added to the water. It can be added as dry powder that is made mixable to the sample, for example, by placing it beforehand into the sampling dish or sampling syringe. If possible, the flow of sterile gas can also be used for the mixing of the sample.

In many cases, it has been found out that the use of the PMEU in the enrichment cultivation of bacteria helps intestinal bacteria (Pesola & Hakalehto, 2011) and bacteria of environmental samples (Hakalehto, 2010) to begin their growth process (in microbe cultivation, "growth" is referred to as the accumulation of the number of individuals or cells). The starting of growth has been shown to be in connection with the growth verification of pathogens, such as *salmonella* (Hakalehto et al., 2007) and campylobacteria (Pitkänen at al., 2009) as well as of indicator species (Hakalehto, 2011), and this has been shown to be in connection with the gas phase used during the cultivation. This can be applied to the use of microbiologic general substrate and selective substrate, such as Colilert™ liquid-broth (Idexx Inc., USA) in water microbiology and other hygiene research (Hakalehto, 2010). This Colilert™ method could have been used effectively also in Finland in the case of Nokia in 2007, especially together with PMEU and automated sampling connected to it.

If the automatic sampling system is, however, connected to a cultivation system were the gas bubbling of the substrates is not in use or it has not been taken into consideration, it is possible to equip these systems with the possibility of extended cultivation or the division of the sample for studies using several different cultivation methods. It is typical for all microbiological analyses that substrate is added to the samples in order to increase growth. The leading of gas to the cultivation is an advantageous way to activate and accelerate growth (Hakalehto et al., 2007; Pitkänen et al., 2009; Hakalehto, 2011). In actual fact, a liquid sample, like a water sample, that is lead into the sample mixture comes to contact with the gas volume that it displaces. In order to guarantee the correctness of the cultivation, the gas must be entirely sterile and, as presented above, a suitable gas flow would be advantageous for the reviving of microbes in the sample. According to previous experimental results, this would guarantee a true to life impression of coliforms, enterobacteria and various types of pathogens in the sample. The gas that is emitted from the cultivations has been successfully used in the detection of indicators and pathogens (Hakalehto et al., 2009). In addition, on the basis of unpublished project results the monitoring of heterotroph microbe flora of waterworks and water intake works should be valued because hygiene indicators alone do not reveal all contaminations (Hakalehto, 2010). Likewise, on the grounds of partly unpublished results of Finnoflag Oy, the use of the Colilert™ method operates, at least just as well in both gasified and static cultivations also from the perspective of growth rate. The results of the national Polaris-project which support this observation have been published for the first time in the home page of Samplion Oy in the lecture material of Elias Hakalehto. The presentation was held at the Veden Vaarat (Dangers in Waters) Seminar on Aug. 26, 2010, in Tampere, where authorities and waterworks were represented and the material is published on the Samplion Oy home page www.samplion.fi.

The significance of the detection of coliform bacteria, and especially the *Escherichia coli* bacterium is central in the microbiological hygiene control of water, and the use of gases in the utilization of the Colilert™ method and other corresponding methods will have an important meaning for it. The implementation of a microbiological testing method resembling the one mentioned above for detecting coliform and *E. coli* has been validated in spring 2010 by Valtion Teknillinen Tutkimuskeskus (the Technical Research Centre of Finland; VTT Expert Services) in Espoo (Wirtanen & Salo, 2010). The Colilert™ method and the liquid-broth media used with it are based in part on the use of antibiotics as a selective feature in substrate liquids and cultivation. On the other hand, the gasifying of the culture media that takes place in PMEU cultivation has a significant influence on the efficacy of the selective effect. In joint projects of THL (the National Institute for Health and Welfare, Finland) and Finnoflag Oy it was noted that, for example in the detection of campylobacteria from water samples, the selectivity of antibiotics increased due to gas bubbles (Pitkänen et. al., 2009). Because of this, it would be advantageous to reduce the level of antibiotics in the guidelines of the use of Colilert™ culture media to gain an optimal result in terms of growth speed. These concentration levels are, however, the manufacturer's proprietary information and are included in many detection methods based on existing norms. However, the reduction of antibiotic concentration can be regarded as potentially advantageous especially, for example, in the case of Colilert™ media and other similar selective culture media. Relating to this, the use of gases in and/or leading of gases into cultivation containers is advantageous both to ensure the start of microbe growth and to optimize the speed of it. Both of these factors continue to have significance in the prevention of hygienic catastrophes such as the one that happened in Nokia in 2007 and in similar smaller water service related cases. For example, in The Netherlands, legislator has required that water authorities and parties involved in producing water must use the best available technology to ensure water quality. Thus, if cultivation is implemented or has to be implemented without a gas flow and bubbling by gas, there is good reason to assume and require that the available knowledge of the effect of gases on different bacteria and most specifically to *E. coli* and other coliforms should carefully be considered and exploited in the application of the culture, culture media or sample. One possibility in practical field work is to dilute selective culture broths containing antibiotics, i.e. culture media, with other culture media for PMEU cultivations, in which case the benefits of the gas flows can maximally be taken into use. Another possibility, as explained above, is a meeting for example with the company Idexx or other manufacturers of culture media in order to modify the concentration of the culture broth.

As different studies have regularly come to the conclusion that both the leading of gas into a cultivation and the gas condition in the cultivation at the beginning of growth are meaningful in the detection of various bacteria and other microbes in laboratory studies (Hakalehto, 2010; Hakalehto, 2011), it can be thought that the consideration of this matter is advantageous in water control where several bacterial strains or single cells are subject to considerable "environmental stress". The flowing speed, pressure, composition and temperature of the gas are meaningful for microbial growth and the start of it. For example, it has been noted that the carbon dioxide level of the sample or gas condition has a role regarding the maximum correctness of the results of the analysis in spite of whether sampling is manual or automatic. Thus, in order to succeed in getting results, it is important to prepare for the arrangement of gas flow or gasifying during sampling and/or starting and execution of the cultivation.

DESCRIPTION OF THE INVENTION

In the microbial control of water intake works, waterworks and water distribution networks, and with all liquid products and processes alike, there may be situations in which it is advantageous to take automatic water samples. This makes it possible to arrange a so-called "early warning" type of alarm as early as possible. This alarm may have multiple stages, for example:
1. physical and chemical criteria
2. static cultivation in a cultivation device of an automatically collected microbiological sample
3. cultivation according to the PMEU method in which the start and speed of the growth of the microbiological sample is tried to be optimized to gain as reliable results as possible A positive indication from the "alarm stage" can automatically initiate the sampling at the following stage. Simultaneously, the remote warning and alerting of people that are responsible for operations can be done, for example, by using a computer network or telecommunication network. Apart from the last stage in which the detection of heterotrophic microbes is advantageous to be performed, cultivation can also be done already on the second stage with the help of gas flow, if it is seen necessary. In this case it is advantageous to use the Colilert™ media or similar antibiotics containing selective culture media and different markers or marking methods to detect coliform bacteria, for example. It is especially important that during sampling, which process includes the adding of culture media into the sample either in a dry or liquid form and possibly in a concentrated form, the differences of pressure and other factors caused by gases during the adding of and/or mixing of substances does not inhibit microbe growth as the focal objective of this method is the detection of microbes.

When samples are collected into containers, test tubes or PMEU syringes or similar, in automatic sampling, it is also possible to rinse in advance the container, test tube, syringe or similar into which the samples are collected with an appropriate gas. In this case it is possible to take into consideration for example the promoting effect of carbon dioxide on the start of microbe growth in certain conditions, or possibly the positive effect of the use of hydrogen gas to the growth of some microbes in small concentrations (Hakalehto, 2011). Thus in automated sampling it is advantageous to construct the device in such a way that the mixing of the culture media and the sample does not cause additional stress to the cells, which are to be detected, in the sample. Gas already existing in the sample, rinsing with gas or leading gas into the culture during sampling or the various cultivation stages, can be used to help sample collection. The method and device according to this invention may contain advantageously one or more bottles of pressurized gas and/or gas mixture which are exploited in a controlled manner regardless of whether the sample is taken on a selective Colilert™ media or similar or a general media that allows the growth of heterotrophic bacteria or other microbes. Alternatively, the cultivation containers, test tubes, syringes or similar that are placed in the microbe cultivation device can in advance be rinsed with an appropriate gas or gas mixture regardless of whether they contain selective factors for a certain culture media or not, or in general regardless of whether they contain culture media in solid or liquid form. This operation can be performed, and in many cases is advantageous to perform, in both static and for example bubbled cultivations, such as the PMEU cultivation. When the sampling is arranged in a manner that gas conditions in connection with it are as preferable as possible to the start of the microbe growth, the result is as optimal as possible regardless of whether aerobic, microaerobic or anaerobic gas is used in the actual cultivation, or whether the cultivation is partly or in full done in a static cultivation or in full, for example, in a PMEU type cultivation arrangement. The information that is gained from the water sample in advance or afterwards as well as information at time of sampling may guide the use of the carrier gas in the sampling in terms of pressure, flow, composition, concentration, temperature or other parameters.

REFERENCES

Hakalehto, E. 2006. Semmelweis' present day follow-up: Updating bacterial sampling and enrichment in clinical hygiene. Review Article. *Pathophysiology* 13(4), 257-67.

Hakalehto, E. 2010. Hygiene monitoring with the Portable Microbe Enrichment Unit (PMEU). $41^{st}$ R3—Nordic Symposium. Cleanroom technology, contamination control and cleaning. Espoo, Finland, May 2010. VTT (State Research Centre of Finland) Publications 266.

Hakalehto, E. 2011. Simulation of enhanced growth and metabolism of intestinal *Escherichia coli* in the Portable Microbe Enrichment Unit (PMEU). In M. C. Rogers and N. D. Peterson (Eds.), *E. coli* infections: causes, treatment and prevention. Nova Publishers, E. Humppi T, Paakkanen H. 2008. Dualistic acidic and neutral glucose fermentation balance in small intestine: Simulation in vitro. *Pathophysiology* 15 (4), 211-220.

Hakalehto E, Pesola J, Heitto A, Bhanj Deo B, Rissanen K, Sankilampi U, Humppi T, Paakkanen H. 2009. Fast detection of bacterial growth by using portable microbe enrichment unit (PMEU) and ChemPro100i® gas sensor, *Pathophysiology* 16: 57-62.

Hakalehto E, Pesola J, Heitto L, Närvänen A, Heitto A. 2007. Aerobic and anaerobic growth modes and expression of type 1 fimbriae in *Salmonella, Pathophysiology* 14: 61-69.

Heitto L, Heitto A, Hakalehto E. 2009. Tracing wastewaters with faecal enterococci. A poster. Second European large lakes symposium. 10-14 August, Nontälje, Sweden.

Pesola J, Vaarala O, Heitto A, Hakalehto E. 2009. Enrichment in Portable Enrichment Unit in rapid characterization of infant intestinal enterobacterial microbiota. *Microbial Ecology in Health and Disease* 21: 203-210.

Pesola, J. & Hakalehto, E. 2011. Enterobacterial Microflora in Infancy—A Case Study with Enhanced Enrichment. *Indian Journal of Pediatrics*. DOI: 10.1007/s12098-010-0341-5Online First™

Pitkänen T, Bräcker J, Miettinen I, Heitto A, Pesola J, Hakalehto E. 2009. Enhanced enrichment and detection of thermotolerant *Campylobacter* species from water using the Portable Microbe Enrichment Unit (PMEU) and real-time PCR, Can J Microbiol 55: 849-858.

Wirtanen, G. & Salo, S. 2010. PMEU-laitteen validointi koliformeilla (Validation of PMEU equipment with coliforms). Report VTT-S-01705-10, VTT. Expert Services Oy, Espoo, Finland.

The invention claimed is:

1. A method to detect microbes from water samples using cultivation, said method comprising the steps of:
   a) collecting at least one microbiological sample in at least one container;
   b) introducing a gas into said container to promote microbe growth in said sample collected in said container;
   c) performing step b) at a time selected from the group consisting of prior to said collecting of said sample, and during said collection of said sample;
   d) starting said microbe growth in said sample in a static cultivation to maximize a division of microbe cells in said sample during a time period to reduce environmental stress on said sample when said sample interacts with said gas;
   e) continuing said static cultivation in a Portable Microbe Enrichment Unit (PMEU) device with an application of a cultivation gas flow so that a transfer from said gas used in said step (b) to said cultivation gas flow is at a condition determined to said microbe cells in a static state;
   f) monitoring at least one hygiene indicator; and
   g) detecting at least one microbe from said sample;

wherein said gas is selected from the group consisting of carbon dioxide and hydrogen.

2. The method according to claim 1, wherein a broth media is used in said static cultivation of microbes, said broth media contains antibiotic factors for said static cultivation and for detection of coliform bacteria.

3. The method according to claim 2, wherein said antibiotic factors of said broth media is configured so that an antibiotic concentration of one of said gas used in step (b), and gas bubbling implemented during said static cultivation is decreased so that said antibiotic concentration affects coliform microbe growth.

4. The method according to claim 1, wherein a microbiological media is used for said static cultivation and for detection of heterotrophic bacteria.

5. The method according to claim 1 further comprising the step of rinsing said container prior to said step (b) with one of a rinsing gas, and a rinsing gas mixture.

6. The method according to claim 1, wherein said collection of said sample is implemented automatically.

7. The method according to claim 1, wherein said gas is introduced into said container from at least one pressurized gas bottle, said cultivation gas is introduced into said PMEU from at least one pressurized gas bottle.

8. The method according to claim 7 further comprising the step of controlling said introducing of said gas using an automatic control system dependent on information available at a period selected from the group consisting of in advance of said sample collection, afterwards from said sample collection, and at a time of said sample collection, said information is used to guide one of a pressure, a flow, a composition, a concentration, and a temperature of said gas used in said collection.

* * * * *